United States Patent [19]
Calello et al.

[11] Patent Number: 5,607,665
[45] Date of Patent: Mar. 4, 1997

[54] NAIL ENAMEL COMPOSITIONS CONTAINING SILICONE GLYCOL COPOLYMERS

[75] Inventors: Joseph F. Calello, Unioni; Robert W. Sandewicz, Spotswood; Anjali A. Patil, Westfield, all of N.J.

[73] Assignee: Revlon Consumer Products Corporation, New York, N.Y.

[21] Appl. No.: 356,994

[22] Filed: Dec. 16, 1994

[51] Int. Cl.$^6$ ............................................. A61K 7/043
[52] U.S. Cl. ............................................. 424/61; 106/3
[58] Field of Search ............................... 424/61; 106/3

[56] References Cited

U.S. PATENT DOCUMENTS

| | | | |
|---|---|---|---|
| 3,746,653 | 7/1973 | Churchfield | 252/321 |
| 3,767,443 | 10/1973 | Clark et al. | 106/291 |
| 3,846,329 | 11/1974 | Householder | 252/358 |
| 3,867,188 | 2/1975 | Campbell | 428/290 |
| 4,166,110 | 8/1979 | Isobe et al. | 424/61 |
| 4,218,250 | 8/1980 | Kasprzak | 106/3 |
| 4,413,086 | 11/1983 | Chang et al. | 524/386 |
| 5,085,694 | 2/1992 | Cifuentes | 106/3 |
| 5,191,002 | 3/1993 | Davis | 106/3 |
| 5,216,033 | 6/1993 | Pereira | 514/844 |
| 5,225,195 | 7/1993 | Soyama | 424/401 |
| 5,284,510 | 2/1994 | Levy | 106/287.14 |
| 5,342,536 | 8/1994 | Miner | 252/162 |
| 5,356,616 | 10/1994 | Sojka | 424/61 |

OTHER PUBLICATIONS

Dow Corning, Additive 54 Product Bulletin 1993.
Dow Corning Formulation Aid 3225C 1984.

*Primary Examiner*—Amy Hulina
*Attorney, Agent, or Firm*—Julie Blackburn

[57] ABSTRACT

A nail enamel composition comprising:
  a) 0.1–85% solvent,
  b) 0.1–60% film former, and
  c) 0.005–5% of a silicone glycol copolymer.

15 Claims, No Drawings

NAIL ENAMEL COMPOSITIONS CONTAINING SILICONE GLYCOL COPOLYMERS

TECHNICAL FIELD

The invention is in the field of compositions for application to human nails.

BACKGROUND OF THE INVENTION

In the recent decades, nail enamels have been radically improved in terms of wear, gloss, ease of application, and other characteristics. Still there is always room for improvement in these characteristics. It has most unexpectedly been discovered that the addition of silicone glycol copolymers to nail enamel formulations will significantly improve gloss and shine, ease of laydown, as well as enhance wear.

SUMMARY OF THE INVENTION

The invention is directed to a nail enamel composition which is removed from the nail only with organic-solvent based removers comprising:

a) 0.1–85% solvent,
b) 0.1–60% film former, and
c) 0.005–5% of a silicone glycol copolymer.

DETAILED DESCRIPTION

The silicone glycol copolymers of the invention are polymethylsiloxanes wherein a portion of the methylsiloxane units are substituted with polyalkylene glycol ether moieties. Preferred is wherein about 60–90% of the compound is polydimethylsiloxane or polyhydrogenmethylsiloxane, and 30–40% of the compound is di-methyl or hydrogen-methyl siloxane units substituted with polyalkylene glycol ethers.

The most preferred silicone glycol polymers have a viscosity ranging from about 1.0 to 500,000, preferably 1.0 to 2,000 cs. at 25° C., a specific gravity ranging from 0.80 to 1.030 at 25° C. and comprise approximately 80% dimethylsiloxane units and 20% propylene oxide substituted methyl siloxane units. Silicone glycol copolymers having this description are commercially available from a variety of sources including Dow Corning under the tradenames Dow Corning Additive 3, 7, 11, 14, 18, 21, 24, 26, 28, 29, 51, 54, 56, 57 and 1248. Particularly preferred is a dimethyl or methyl-hydrogen polysiloxane substituted with propylene glycol mono-allyl ether in particular, the reaction products of dimethyl, methyl hydrogen siloxane and polypropylene glycol mono-allyl ether.

The solvents in accordance with the invention may be water or non-aqueous solvents. Water based nail enamels largely contain water rather than the traditional organic solvents (although water based nail enamels may contain small amounts of organic solvents). Suitable organic solvents include alkyl acetates such as methyl, ethyl, propyl, isopropyl, and butyl acetates; $C_{1-10}$ straight or branched chain alcohols such as methyl, ethyl, propyl, isopropyl, butyl, hexyl alcohols; various aliphatic or aromatic ketones such as acetone, methyl ethyl ketone, etc.; aliphatic citrates, toluene, ethers of glycol, and mixtures thereof. The solvents used will depend on whether the nail enamel composition is water or solvent based.

Suitable film formers will vary. For solvent based nail enamels nitrocellulose is the film former of choice, but other cellulose derivatives such as cellulose acetate butyrate, cellulose acetate propionate, etc., as well as polyurethanes, polyurethane-acrylics, acrylics, styrene-acrylates, acrylates, vinyls, acrylonitrile/butadiene copolymers, styrene/butadiene copolymers, polyvinylbutyral resins, epoxies and mixtures thereof, as well as the copolymers disclosed in U.S. Pat. No. 4,762,703 which is hereby incorporated by reference:

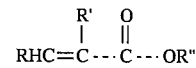

wherein R is H; $CH_3$; $C_2H_5$; R' may be H; $CH_3$ to $C_4H_9$; and R" may be:

(i) $CH_3$ to $C_4H_9$ straight chain alcohols;

(ii) saturated or unsaturated cyclic alcohols containing up to 20 carbon atoms;

(iii) $C_3H_7$ to $C_{16}H_{37}$ branched alkyl or $C_5H_{11}$ to $C_{22}H_{45}$ straight chain alkyl alcohols; and $C_{22}H_{45}$ straight chain alkyl alcohols; and (iv) alkoxy or aryloxy alkyl alcohols. For water based nail enamels, the preferred polymers are of the formula:

copolymer having a glass transition temperature of −10° to 50° C. obtained by the polymerization of two or more of the following monomers, at least one of which is of formula I or formula II (hereinafter "Polymer I"):

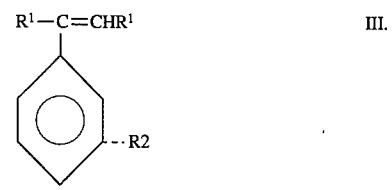

wherein each R is independently hydrogen $C_{1-20}$ alkyl, phenyl, benzyl, hydroxy-$(C_{1-4})$-alkyl, $C_{1-4}$ alkoxy-$(C_{1-4})$alkyl, cyclopentyl, cyclohexyl, furyl, $C_{1-4}$ alkylfuryl, tetrahydrofuryl, or $C_{1-4}$ alkyltetrahydrofuryl; $R^1$ is independently hydrogen or methyl, and $R^2$ is independently hydrogen or $C_{1-3}$ alkyl, subject to the limitation that when R in one of the monomers is $C_{1-4}$ alkoxy-$(C_{1-4})$alkyl, then R in the other monomer is a group other than $C_{1-4}$ alkoxy-$(C_{1-4})$alkyl or hydroxy-$(C_{1-4})$alkyl. These copolymers may be used alone or in conjunction with a second polymer which is a homo- or copolymer of polyurethane, a water dispersible rosin ester, a water reducible alkyd, a polyester, polyvinylbutyral resin, polyamide, or mixtures thereof (hereinafter referred to as "Polymer II"). Preferred water based nail enamel compositions are comprised of a mixture of Polymers I and II. Such nail enamel compositions are disclosed and claimed in copending patent application entitled "Aqueous Based Nail Enamel Compositions" by inventors Patil, et al., U.S. Ser. No. 357,005, filed Dec. 16, 1994, which is hereby incorporated by reference.

The preferred waterborne nail enamels in accordance with the invention comprise:

16–60% Polymer I, 0.1–10% Polymer II,

10–85% water, and 0.005–5% silicone glycol copolymer.

The compositions may contain 0.1–30% coalescents and 0.1–40% pigments. Suitable coalescents include glycol ethers such as $C_{1-10}$ straight or branched chain alkyl glycol alkyl ethers such as propylene glycol (methyl, ethyl, propyl, butyl, hexyl, etc) ether, $C_{1-10}$ straight or branched chain alkyl ether acetates such as butylene, ethylene, and propylene glycol ether (methyl, ethyl, propyl, or butyl acetates), di-$C_{1-10}$ alkyl ether acetates such as dipropylene glycol ether acetate, dialkyl glycol ethers such as diethylene glycol ethers (mon- or di- methyl, ethyl, propyl, butyl, hexyl, phenyl), $C_{1-10}$ alkyl glycol phenyl ethers such as propylene glycol phenyl ether, aromatic based glycol ethers, methyl propanediol, N-methyl pyrrolidone, gamma butyrolactone, benzyl alcohol, diacetone alcohol, alkyl acetates, propylene glycol n-butyl ether, dipropylene glycol tertiary butyl ether, dipropylene glycol methyl ether, dipropylene glycol propyl ether, tripropylene glycol methyl ether, ester alcohols, and mixtures of these compounds.

Suitable pigments are inorganic or organic pigments known as the FD&C and D&C colors, lakes, iron oxides, and so on. Such pigments are disclosed in the *C.T.F.A. Cosmetic Ingredient Handbook*, First Edition, 1988, which is hereby incorporated by reference.

The waterborne composition may also contain 0.1–10% rheology modifiers. Ingredients which fit into this category include hydrophobically modified polyurethanes such as those disclosed and claimed in U.S. Pat. No. 4,155,892 which is hereby incorporated by reference.

It may also be desired to add wetting agents or surfactants. If present, 0.01–20%, preferably 0.1–10% wetting agent is suggested.

The other preferred nail enamel composition of the invention is a solvent based nail enamel comprising:

a) 0.1–85% nonaqueous solvent, b) 0.1–60% film former, and c) 0.005–5% of a silicone glycol copolymer, and d) 0.01–40% plasticizer Suitable plasticizers are glyceryl, glycol, or citrate esters as set forth in U.S. Pat. No. 5,066,484 which is hereby incorporated by reference. In addition, the composition may also contain 0.1–40% pigment and 0.01–5% suspending agent. Suitable pigments are the D&C and FD&C colors. Suspending agents are the montmorillonite minerals and other suspending agents known in the art.

The invention will be further described in connection with the following examples which are set forth for the purpose of illustration only.

EXAMPLE 1

An aqueous nail enamel composition was made as follows:

| | w/w % |
|---|---|
| Acrylic aqueous emulsion (46% solids) | 61.1 |
| Aqueous polyurethane dispersion (35% solids) | 24.1 |
| 2,2,4-trimethyl 1,3-pentanediol monoisobutyrate | 10.4 |
| Silicone glycol copolymer (10%) | 0.4 |
| Pigment | 4.0 |

The above nail enamel was applied to nails and provided a smooth, high gloss finish.

EXAMPLE 2

Nail enamel compositions were made as follows:

| | w/w % | | |
|---|---|---|---|
| | 1 | 2 | 3 |
| Nitrocellulose base | 94.02 | 89.02 | 89.02 |
| Ethyl acetate | 1.00 | 5.50 | 6.00 |
| Pigment | 4.98 | 4.98 | 4.98 |
| Silicone glycol copolymer (10%) | 0 | 0.50 | 0 |

EXAMPLE 3

Compositions 1–3 of Example 2 were tested on eight panelists. The test subjects were instructed to apply two coats of test and control nail enamel to alternate fingernails and rate application, dry time, bubbling, appearance, gloss, and wear after four days. Wear was evaluated by determining the amount of nail enamel which had worn off the nail after each day and rating the results on a 1 to 10 scale, with 10 being best and 1 being worst. The results are set forth below:

| | Example 2 | | |
|---|---|---|---|
| Test Day | 1 | 2 | 3 |
| 1 | 8 | 9 | 8 |
| 2 | 7 | 8 | 7 |
| 3 | 6 | 8 | 6 |
| 4 | 1 | 6 | 3 |

The results show that number 2, containing silicone glycol copolymer, provided substantially better wear than numbers 1 and 3 which did not contain the silicone glycol copolymer. In addition, panelists rated application, dry time, bubbling, appearance, and gloss as better than average.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. An aqueous based nail enamel composition comprising, by weight of the total composition:

16–60% of a polymer selected from the group consisting of polyacrylate-methacrylate copolymers, an acrylic acid homopolymer, a methacrylic acid homopolymer, an acrylate-styrene copolymer, and mixtures thereof, 0.1–10% polyurethane, 10–85% water, and 0.005–5% silicone glycol copolymer.

2. The composition of claim 1 further comprising 0.01–15% pigment.

3. The composition of claim 1 further comprising 0.01–30% coalescent.

4. The composition of claim 3 wherein the coalescent is a glycol ether, a $C_{1-10}$ straight or branched chain alkyl ether acetate, a di-$C_{1-10}$ alkyl ether acetate, a dialkyl glycol ether, a $C_{1-10}$ alkyl glycol phenyl ether, an aromatic based glycol ether, methyl propanediol, N-methyl pyrrolicdone, gamma butyrolactone, benzyl alcohol, diacetone alcohol, alkyl acetates, propylene glycol n-butyl ether, dipropylene glycol tertiary butyl ether, dipropylene glycol methyl ether, dipropylene glycol propyl ether, tripropylene glycol methyl ether, ester alcohols, and mixtures thereof.

5. The composition of claim 3 further comprising 0.1–10% rheology modifier.

6. The composition of claim 3 further comprising 0.01–20% wetting agent.

7. A solvent based nail enamel composition which is removed from the nail only with organic solvent-based removers, consisting essentially of, by weight of the total composition:

a) 0.1–85% of a non-aqueous solvent, b) 0.1–60% nitrocellulose, c) about 0.005–0.5% of a silicone glycol copolymer which is the reaction product of dimethyl methyl hydrogen siloxane and polypropylene glycol monoallyl ether wherein about 60–90% of the copolymer is dimethyl methyl hydrogen siloxane and 30–40% of the copolymer is polypropylene glycol monoallyl ether, and d) 0.01–40% of a plasticizer which is a glyceryl, glycol, or citrate ester.

8. The nail enamel composition of claim 7 wherein the non-aqueous solvent is an alkyl acetate, $C_{1-10}$ straight or branched chain alcohol, an aliphatic or aromatic ketone, aliphatic citrates, toluene, glycol ether, or mixtures thereof.

9. The nail enamel composition of claim 8 wherein the non-aqueous solvent is methyl acetate, ethyl acetate, propyl acetate, isopropyl acetate, butyl acetate, methyl alcohol, ethyl alcohol, propyl alcohol, isopropyl alcohol, butyl alcohol, hexyl alcohol, butyl acetate, acetone, methyl ethyl ketone, toluene, glycol ether, or mixtures thereof.

10. The nail enamel composition of claim 7 wherein the film former is nitrocellulose, cellulose acetate isobutyrate, cellulose acetate propionate, or mixtures thereof.

11. The nail enamel composition of claim 7 additionally comprising 0.1–40% pigment.

12. A solvent based nail enamel composition which is removed from the nail only with organic-solvent based removers, consisting essentially of, by weight of the total composition:

0.1–85% of a non-aqueous solvent selected from the group consisting of an alkyl acetate, acetone, methyl ethyl ketone, toluene, an aliphatic citrate, or mixtures thereof, 0.1–60% nitrocellulose, 0.005–5% of a silicone glycol copolymer which is the reaction product of dimethyl, methyl hydrogen siloxane and polypropylene glycol monoallyl ether wherein about 60–90% of the copolymer is dimethyl, methyl hydrogen siloxane and 30–40% of the copolymer is polypropylene glycol monoallyl ether, and 0.1–40% of a plasticizer which is a glyceryl, glycol, or citrate ester.

13. The composition of claim 12 additionally comprising 0.1–40% pigment.

14. The composition of claim 13 wherein the pigments are iron oxides.

15. The composition of claim 14 wherein the silicone glycol copolymer is present at about 0.005 to 0.05% by weight of the total composition.

* * * * *